United States Patent
Townsend-Hansen

(10) Patent No.: US 6,746,241 B2
(45) Date of Patent: *Jun. 8, 2004

(54) ORTHODONTIC BRACKET

(76) Inventor: Shelly Townsend-Hansen, 2902 26th Ave. SW., Fargo, ND (US) 58103

( * ) Notice: Subject to any disclaimer, the term of this patent is extended or adjusted under 35 U.S.C. 154(b) by 0 days.

This patent is subject to a terminal disclaimer.

(21) Appl. No.: 10/039,202

(22) Filed: Jan. 4, 2002

(65) Prior Publication Data

US 2002/0058227 A1 May 16, 2002

Related U.S. Application Data

(63) Continuation of application No. 09/425,809, filed on Oct. 25, 1999.
(60) Provisional application No. 60/105,791, filed on Oct. 27, 1998.

(51) Int. Cl.$^7$ ................................................. A61C 7/00
(52) U.S. Cl. ........................................................ 433/8
(58) Field of Search ........................... 433/8, 9, 10, 11, 433/18, 24, 22, 17

(56) References Cited

U.S. PATENT DOCUMENTS

| | | | |
|---|---|---|---|
| 3,835,538 A | 9/1974 | Northcutt | 433/9 |
| 4,386,909 A | 6/1983 | Hanson | 433/20 |
| 4,415,330 A | 11/1983 | Daisley et al. | 433/16 |
| 4,655,707 A | 4/1987 | Chasanoff | 433/9 |
| 5,395,237 A | 3/1995 | Pospisil et al. | 433/8 |
| 5,607,299 A | 3/1997 | Nicholson | 433/3 |
| 5,810,584 A | 9/1998 | Wong | 433/9 |
| 5,954,502 A | 9/1999 | Tuenge et al. | 433/16 |

OTHER PUBLICATIONS

"Treatment Strategy", Chapter 4, pp. 43–53 in The Orthodontic Treatment of Impacted Teeth, Adrian Becker, Mosby 1998.

*Primary Examiner*—Kevin Shaver
*Assistant Examiner*—Melba Bumgarner
(74) *Attorney, Agent, or Firm*—Fredrikson & Byron, P.A.

(57) ABSTRACT

An orthodontic bracket for providing traction to an impacted tooth, the bracket having a base portion adapted to be fixed to the exposed tooth surface, and a plurality of attachment points adapted to be attached to one or more traction ligatures (e.g., elastic modules), which in turn are adapted to be attached to an arch wire in order to provide traction forces to the tooth.

15 Claims, 2 Drawing Sheets

ORTHODONTIC BRACKET

CROSS REFERENCE TO RELATED APPLICATIONS

The present application is a continuation of U.S. patent application filed Oct. 25, 1999 and assigned Ser. No. 09/425,809, which is a continuation of U.S. patent application filed Oct. 27, 1998 and assigned Serial No. 60/105,791 filed Oct. 27, 1998, the entire disclosure of which is incorporated herein by reference.

TECHNICAL FIELD

The present invention relates to the field of orthodontics, and in particular to orthodontic brackets. In a related aspect, the invention relates to orthodontic methods and materials for the treatment of impacted teeth.

BACKGROUND OF THE INVENTION

Orthodontia generally involves the treatment of malocclusions by the use of fixed appliances such as brackets and archwires. The teeth can be initially leveled by the use of an archwire of standardized archform and a given coefficient of elasticity. Later, heavier archwires can be substituted to perform root movements necessary for achieving optimal results.

A wide variety of types and styles of orthodontic brackets are available today, including those available from 3M Unitek (e.g., "Victory" series brackets, as described in U.S. Pat. No. 5,395,237), and from Ormco Corporation. Ormco, for instance, markets its "minidiamond" line of brackets, which are described as being related to U.S. Pat. No. 4,415,330. The '330 patent provides an orthodontic bracket assembly adapted for use with an arch wire in straightening a tooth having a crown long axis preferably disposed at a particular angle with respect to an occlusal plane.

When dealing with a malocclusion that involves one or more impacted teeth, various modifications or additional steps must be made to the general procedure. The treatment of impacted teeth typically includes surgical exposure followed by excision, spontaneous eruption or, more commonly, orthodontic traction. See, generally, "Treatment Strategy", Chapter 4, pp 43–53 in The Orthodontic Treatment of Impacted Teeth, Adrian Becker, Mosby 1998.

The ectopic eruption and impaction of the permanent maxillary canine is a frequently encountered clinical problem whose treatment requires the cooperation of several dental specialties, particularly oral surgery and orthodontics. The incidence of this problem is between one percent and two percent of the population, with palatal impaction occurring in about 85% of the cases and buccal impaction in about 15% of the cases.

The cause of impaction is considered to be multifactorial, with local causes being the most common. These would include tooth size-arch length discrepancies, prolonged retention or early loss of deciduous canines, abnormal position of the tooth germ, alveolar cleft, cystic or neoplastic change, root dilaceration, and iatrogenic idiopathic reasons.

The management options for impacted canines depend on the type of impaction (e.g., either buccal or palatal), and the severity of the transplantation, or exposure, with or without orthodontic traction to align the malpositioned tooth. For unerupted teeth, the preferred option is surgical exposure and alignment by traction. Impacted teeth may also erupt ectopically and not need surgical intervention. They would, however, likely still require orthodontic guidance to achieve correct arch positions.

Orthodontic traction, and in particular, the use of attachments in connection with impacted teeth, has evolved over the years. Prior to the 1960's, as described in Becker, it was common to use a lasso wire twisted lightly around an impacted canine. The lasso has since become obsolete, in large part because of the inevitable tendency of the lasso to settle at the narrowest diameter of the tooth, and the frequency of gingival irritation.

Several systems were then developed based on the use of threaded pins. These methods have also not met with widespread use, in view of the difficulties encountered in accessing impacted teeth, the desirability of limiting surgical exposure, and the risk of entering the pulp.

Standard preformed orthodontic bands have been used as well, including Edgewise, Begg and other orthodontic brackets. As explained in Becker, such brackets provide sophisticated designs of attachment that enable the orthodontist to perform any type of movement on a tooth in the three planes of space. It is not possible, however, to achieve more than tipping, extrusion, and some rotation, at least until the bracket reaches and fully engages the arch wire. In turn, the efficacy of such brackets in performing traction is no greater than the use of simple eyelets, as described below. Also, in view of the size and profile of such brackets, they can create irritation and interference when used in such applications.

One current approach that is employed today for the movement of impacted teeth, as described in Becker, includes the use of an eyelet, welded to a band material and used in conjunction with a mesh backing. The relatively small size and low profile allows the eyelet to be positioned in a midbuccal position of even awkwardly positioned teeth, and in a manner that is less irritating to the surrounding tissue. For these reasons, Becker recommends that a small eyelet be used as an initial attachment, at the time of surgery, to be removed (and replaced with a standard bracket) once the tooth has progressed to the point where it comes into close proximity to the archwire. A bonded "button" is commonly also used in this situation. Retention of the elastic ligature is unreliable, however, and the edges can be sharp and irritating for the patient. Unfortunately, elastic modular traction cannot be used alone with the eyelet design to complete orthodontic treatment. Later, a more sophisticated bracket can be used for more intricate root manipulations, including rotating, uprighting, and torqueing.

Along similar lines, Northcutt (U.S. Pat. No. 3,835,538) describes an orthodontic onlay which is cemented directly to an impacted tooth to aid in exerting corrective traction thereon. A curved base surface has a curvature substantially the same as an incisal portion of the tooth involved. The onlay has a series of openings or recesses leading from that surface toward the opposite surface for receiving and holding cement, thereby increasing the bond between the tooth and the onlay when the cement is applied. Bonding strength is increased further by plasma processing the surface, especially when the onlay is made from plastic. On its opposite surface the onlay has means for attaching a ligature. The specialized orthodontic onlay is said to be made of plastic and secured by cement (such as a suitable epoxy cement) directly to the tooth. By use of the onlay, the patent proposes that it would no longer be necessary to remove bone from the entire crown. Instead, a small window incision is sufficient to gain access and to enable the desired traction. The "means" for attaching a ligature are depicted (e.g., in FIG. 2 thereof) as either a plastic loop (25) or a metal member (26), each analogous in shape to a single eyelet.

A significant aspect, and focus, of the onlay described in Northcutt appears to be the method of cementing it onto the tooth. The patent describes the problem of achieving sufficient adhesion to enable small articles to transmit a substantial amount of traction. It addresses that problem by applying cement to the onlay, with the aid of a special plasma-processed surface and a series of openings from the surface to be cemented. The openings, and additional cement, were said to enable a strong 'bonding' force to be applied. For whatever reason, however, to the best of Applicant's knowledge, no such onlay is commercially available today.

Other common approaches, presently employed by Applicant and others, involve the use of a bonded lingual button or makeshift brackets. Conventional brackets, however, tend to have wide, rigid bases as well as a wide, sharp and high profile which can cause irritation as the tooth is drawn through the soft tissues. In turn, it is often difficult or impossible to bond a conventional bracket to the necessary position on an impacted tooth.

While the eyelet described by Becker, and such other approaches, have gained some acceptance, they continue to suffer from considerable drawbacks. Often, for instance, the elastic thread can become disengaged due to poor retention on the eyelet or bracket. Wire chains have similar problems, and have a tendency to pull the bonded bracket off when activated. Hence, these techniques remain cumbersome, inefficient and of questionable utility.

What is clearly needed are new materials and methods for treating impacted teeth, in a manner that avoids the shortcomings of present techniques.

SUMMARY OF THE INVENTION

Figure 1A:
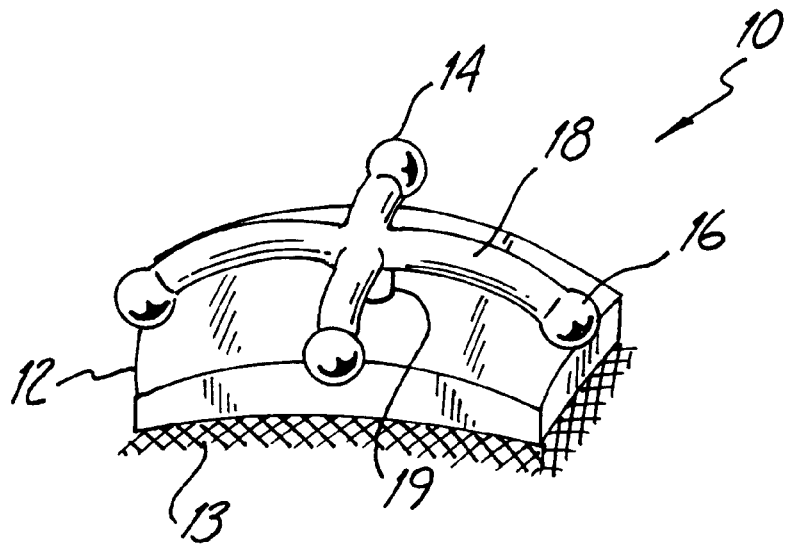
FIGS. 1a and 1b shows top and side perspectives view of a preferred embodiment of the bracket of this invention having a curved pad, low profile and four attachment points.

The present invention provides an orthodontic bracket comprising a base portion for fixing the bracket to a tooth, the base portion having upper and lower major surfaces, the lower major surface being adapted to be contacted with and/or adhered to an exposed (e.g., surgically exposed) surface of an impacted tooth. The upper major surface, in turn, bearing a plurality of attachment points adapted to be releasably attached to one or more traction ligatures (e.g., elastic modules or wire ligatures), which in turn are adapted to be releasably attached to an arch wire in order to provide traction forces to the tooth.

The orthodontic bracket can be used to provide traction forces to a desired extent and a desired direction, e.g., by selection and placement of the bracket itself, as well as the selection of the number and type of ligatures to be used, and their attachment points on both the bracket and the archwire. In turn, the orthodontic bracket, and related system, provides an optimal combination of retention on the tooth, ligature retention, directional control, size, comfort, esthetics, ease of use, efficacy, and cost, as compared to conventional approaches.

The bracket is provided with one or more attachment points, e.g., in the form of hook portions slightly curved toward the gingival surface in order to minimize tissue impingement. Such hooks can take any suitable form, e.g., in the form of standard cuspid hooks, and can be adapted to have any desirable profile (e.g., low to high profile). The hooks can also extend slightly over the bracket base, and are optionally removable at the time of surgery, in order to leave only those hooks necessary for effective traction. For instance, such hooks can be snipped or crimped in order to minimize their ability to impinge upon tissue. In one preferred embodiment, for instance, the attachment points take the form of curved, ball-tipped "stalks", emanating from a common trunk or point attached to the base.

A bracket of this invention can be used as a transition bracket with any impacted tooth, upon surgical or nonsurgical exposure, although it is particularly well suited to the maxillary cuspid. The tooth-contacting surface of the apparatus can be provided in a predetermined shape, e.g., flat or curved, in order to facilitate its use on any possible surface.

The invention provides an orthodontic bracket system for applying corrective or traction forces to impacted teeth. In a preferred embodiment the bracket system includes a bracket for engaging an arch wire in a predetermined, and preferably controllable, manner. In such an embodiment, the bracket is typically attached by means of one or more traction ligatures, such as elastic modules (e.g., chains or threads). In another aspect, the present invention provides a kit that includes a plurality of brackets of the present invention, having varying sizes, profiles, and/or configurations of attachment points.

In another aspect, the present invention includes a bracket as described above, which has been pre-coated with bonding material, and packaged in a form ready for use. A coated bracket of this nature can be used to provide fast, superior, one-step bonding adhesion to the tooth. In yet another aspect, the present invention provides a combination comprising an impacted tooth having adhered thereto a bracket as described above. In a further embodiment, the tooth/bracket combination further includes one or more traction ligatures attaching the combination to an archwire.

DETAILED DESCRIPTION

A bracket of the present invention can be provided having any suitable configuration and dimensions. The base, for instance, can be substantially elliptical, barrel-shaped, rhomboid, square, rectangular, oval, circular or other suitable shape. The base, in turn, can be used with any type of cement material or bonding adhesive, and with any suitable bonding method (e.g., welded to bands). In a preferred embodiment, the bracket base has a substantially barrel-shaped configuration shape, with its longest dimension (to be placed in the mesial/distal direction) between about 1 mm and about 4 mm in length, and preferably between about 2 mm and about 3 mm in length, and an overall tooth-contacting surface area that is comparable to that of a conventional lower anterior bracket, and substantially smaller than that of a conventional cuspid bracket. The profile (including maximum height) of the bracket is adapted to provide minimal irritation, with a maximum attachment point height preferably between about 1 mm and about 4 mm in height, more preferably between about 1 and about 3 mm, and most preferably between about 1 mm and about 2 mm.

The bracket provides a plurality of attachment sites, and preferably between 2 and 10 sites, inclusive, and preferably between 3 and 5 sites or between 4 and 6 sites, inclusive. The attachment sites can, independently, be in any suitable shape and configuration, including loops attached at both ends to the base, or hooks, cleats, and the like. The attachment sites can be individually attached to the base, or two or more can be joined to each other and/or to a common trunk to the base. The attachment sites can also be equally or unequally spaced from each other.

The attachment sites are themselves optionally removable, e.g., able to be crimped or snipped in order to remove those that are not needed as attachment sites in a particular application, thereby minimizing the chance of tissue impingement. The number, orientation, and type of attachment sites are selected to provide an optimal combination of such properties as strength, directional control, spacing, ease of use, minimal irritation, and flexibility.

Traction ligatures suitable for use in combination with the present bracket are commercially available, e.g., from 3M/Unitek as their line of "AlastiK" materials, or from Ormco Corporation, as their line of "power chain", "power thread" and "power tube" products. Such products are typically fabricated from elastic urethane or other polymers, and used conventionally for ligation, consolidation, and anterior retraction.

Figure 1B:
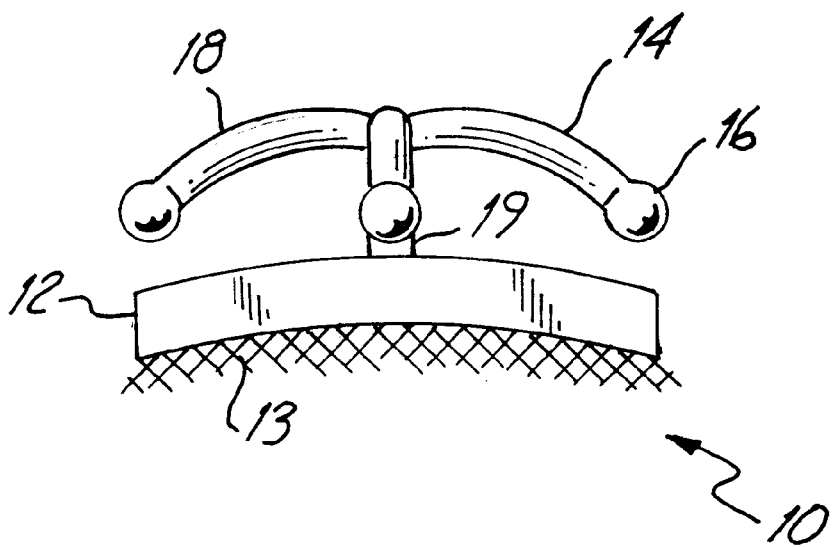

A preferred embodiment of the present invention will be described with reference to the Drawing, where FIGS. 1a and 1b show top and side views, respectively, of a bracket 10 that includes a base portion 12 (showing optional mesh pad 13) and four attachment points 14, for use in attaching one or more traction ligatures (e.g., in the form of elastic modules) for attaching the bracket to an archwire. As shown, the attachment points are each similar in nature, and include terminal attachment points 16 for use in connecting an elastic module (e.g., by hooking, tying, pinching, catching or otherwise restraining the module), and respective arms 18 emanating from a common base 19.

Figure 2A:
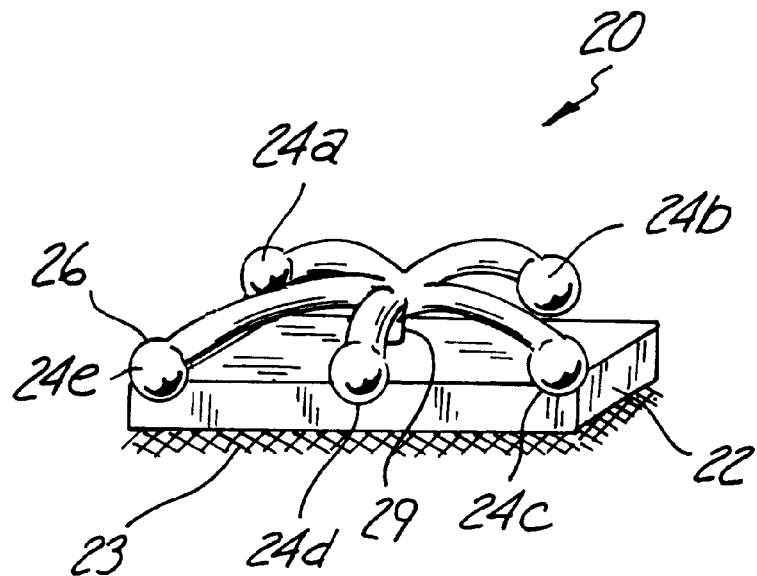
FIGS. 2a and 2b show top and side perspective views of an alternative preferred embodiment of the bracket of the invention having a flat pad, high profile and five attachment points.
Figure 2B:
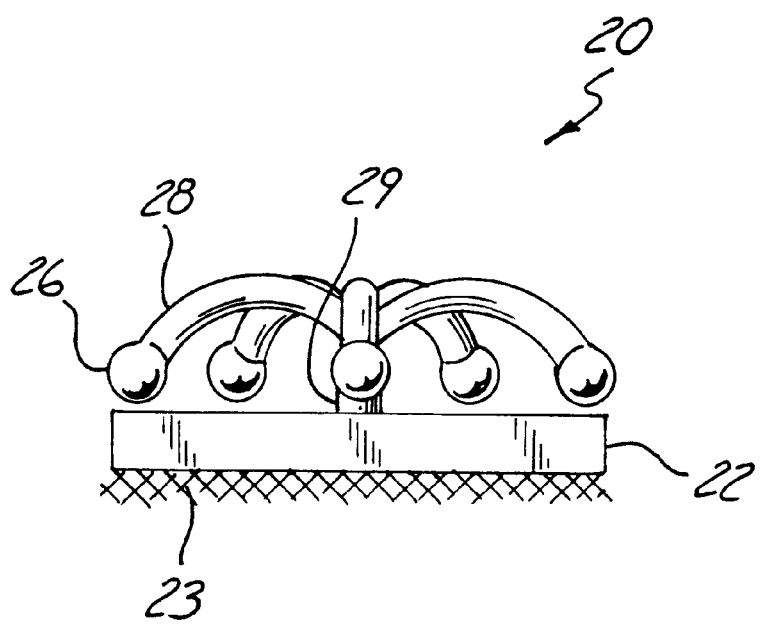

An alternative preferred embodiment is shown in FIGS. 2a and 2b, showing top and side views, respectively, of a bracket 20 having a base portion 22 (showing optional mesh pad 23), five attachment points 24a through 24e. The attachment points each terminate in a respective rounded ball portion 26, attached to base 22 by means of a respective arm 28 emanating from a common base trunk 29.

A bracket of the present invention can be prepared using techniques and materials well within the skill of those in the art, given the present description. Brackets are typically prepared from a material that provides an optimal combination of such properties as esthetics, hygiene, and strength. Examples of such materials include, but are not limited to, stainless steel alloys, ceramics, polycarbonate, and ceramic-polycarbonates. Such brackets can be fabricated by any suitable means, e.g., by welding, casting, sintering, and metal injection molding. Stainless steel alloy attachments are probably the most common types available today, but a clear ceramic or polymeric (e.g., polycarbonate) version of the present bracket can be included as well, e.g., for use with the light-curing system adhesives now available for use in a wet field.

A bracket of the present invention can be attached and used, given the present description, using techniques and materials within the skill of those in the art. In the surgical exposure of an impacted tooth, only enough bone should be removed to allow for the placement of an attachment. Preferably, during the procedure, the cementoenamel junction should not be unintentionally exposed. If surgery is not required to expose the tooth, the orthodontist can immediately place the transition bracket on the impacted tooth.

The surgeon conservatively exposes the impacted tooth. The tissues over the location of the attachment can be excised so that a small portion of enamel is exposed. The site is prepared for the attachment and depends on the adhesion chosen to use with the attachment. Composite resins, which have become the material of choice for bonding brackets, can be used to attach the bracket to the exposed tooth surface. Such resins, however, can include a number of technique-sensitive steps, and typically require a completely dry field of operation from start to finish. The enamel is etched at the bond site leaving a roughened surface suitable for resin infiltration. A primer is placed on the etched enamel surface, and the bonding resin is placed on the bracket. The bracket is positioned on the tooth and allowed to cure chemically or is cured by light irradiation from a dental curing device. Newer, light-cured, resin-reinforced glass ionomer cements can be used as well, and can eliminate the need for working in a dry field.

After the attachment is placed and bonded, one or more ligatures (e.g., wires or elastic chains) are placed over one or more attachment hooks and drawn to the archwire. The surgeon usually determines the initial number and direction of ligations and the orthodontist then continues in that same manner at follow-up appointments. Synthetic elastomeric chains suitable for such purposes are commercially available, while elastic thread or stainless steel ligature wire can also be used. The knot tends to loosen on elastomeric thread, and much of the original force of the tie will be lost with this loosening. Care must be taken using wire ligatures, so that the bond strength of the newly placed attachment will not be seriously tested as the wire is twisted. Optionally, the surgical flaps can be re-laid over the bracket and ligatures connecting the impacted tooth to the archwire.

After time, the impacted tooth should progress to a point where it is in close proximity to the archwire. At that time the orthodontist can remove the transition attachment and replace it with the type of bracket that is being used on the other teeth to permit more precise movement of the tooth (rotating, uprighting, and torqueing).

A kit can include a plurality of brackets of the present invention, having differing combinations of base and attachment point configurations, in order to allow for the unknown during the surgical procedure. Base options can include, for instance, flat pads, curved pads, and optionally, pliable mesh pads. A kit of the present invention can include one or more brackets as described herein, e.g., as plurality of different sizes and/or configurations (e.g., base, number of attachment sites). Optionally, a bracket of this invention can be provided in a form that has bee precoated with a bonding material. Such a pre-coated bracket can substantially reduce the number of steps, and associated time involved in the bonding procedure.

In addition to selecting the appropriate base, the number and orientation of the attachment points (e.g., hooks) can be selected by the surgeon to provide optimal directional control in view of the number and type of ligatures (e.g., elastic modules) to be used. An elastic module chain, for instance, can be easily placed over the appropriate hook and attached to a relatively stiff arch wire. Putting a light wire through the elastic chain can alter the direction of pull to avoid tissue impingement, root resorption of adjacent teeth, or any injury of neighboring teeth. Hook height is typically of a low profile for patient comfort and yet should be long enough for good retention of elastic modules. As the impacted tooth moves toward a better arch position, the clinician can adjust placement of the elastic modules to control the path of eruption at each monthly visit. Fresh elastic modules are placed at each appointment to allow gentle forces (e.g., approximately 2 ounces or 60 grams) for tooth guidance. This allows the orthodontist to control the force magnitude and direction.

The combined effects of light surgical exposure and light orthodontic movements and forces are beneficial to the future periodontal health of the tooth since they minimize the loss of alveolar bone support and potential injury to the tooth during traction. Earlier methods of uncovering impacted canines advocated radical bone removal to expose the crown of the impacted tooth so as to remove all bony obstacles and to provide an easier path for tooth movement. The more bone that is removed initially, the greater the bone loss after orthodontic treatment. Light movements done with elastic modules that can be placed on the present bracket cause significantly less bone loss than heavy movement (torque) during the traction of the impacted tooth. No other transition bracket or attachment available today allows for effective and reliable ligature retention while also providing for the optional use of elastic or wire ligatures.

What is claimed is:

1. An orthodontic bracket comprising a base portion for fixing the bracket to a tooth, the base portion having upper and lower major surfaces, the lower major surface being adapted to be contacted with and adhered to an exposed surface of an impacted tooth, the upper major surface bearing a plurality of attachment points, each adapted to be attached to one or more respective traction ligatures, the traction ligatures, in turn, being adapted to be attached to an arch wire in order to provide traction forces to the tooth, wherein the attachment points are provided in the form of hook portions slightly curved toward the gingival surface with the bracket in position upon the tooth and are in the form of curved, ball-tipped stalks emanating from a common trunk attached to the base portion.

2. A bracket according to claim 1 wherein the bracket is prepared from stainless steel.

3. A bracket according to claim 1 wherein the profile of the bracket is between about 1 mm and about 4 mm in height.

4. A bracket according to claim 3 wherein the bracket is prepared from stainless steel.

5. A bracket according to claim 4 wherein the bracket provides between 3 and 5 attachment sites, inclusive.

6. A bracket according to claim 5 wherein the lower major surface of the base portion comprises a mesh pad.

7. A bracket according to claim 6 further comprising a bonding material pre-coated to the mesh pad positioned upon the base portion of the bracket.

8. A bracket according to claim 5 further comprising a bonding material pre-coated to the base portion of the bracket.

9. A bracket according to claim 3 wherein the bracket is prepared from stainless steel and provides between 3 and 5 attachment sites, inclusive.

10. A bracket according to claim 9, wherein the lower major surface of the base portion comprises a mesh pad.

11. A bracket according to claim 9 further comprising a bonding material pre-coated to the base portion of the bracket.

12. A bracket according to claim 1 wherein the bracket provides between 3 and 5 attachment sites, inclusive.

13. A bracket according to claim 1, wherein the lower major surface of the base portion comprises a mesh pad.

14. A bracket according to claim 13 further comprising a bonding material pre-coated to the mesh pad positioned upon the base portion of the bracket.

15. A bracket according to claim 1 further comprising a bonding material pre-coated to the base portion of the bracket.

* * * * *